United States Patent [19]

Schneider

[11] Patent Number: 4,578,062
[45] Date of Patent: Mar. 25, 1986

[54] INTRAVENOUS CATHETER HOLDER

[76] Inventor: Paul E. Schneider, 300 N. Main St., Woodsfield, Ohio 43793

[21] Appl. No.: 681,801

[22] Filed: Dec. 14, 1984

[51] Int. Cl.$^4$ .......................... A41D 1/04; A61M 5/00
[52] U.S. Cl. ................................ 604/174; 2/DIG. 7; 128/DIG. 26
[58] Field of Search ............ 2/DIG. 7; 604/174, 179; 128/DIG. 26

[56] References Cited

U.S. PATENT DOCUMENTS

| | | | |
|---|---|---|---|
| 3,464,063 | 9/1969 | Hoegerman | 2/DIG. 7 |
| 3,490,072 | 1/1970 | Keltner | 2/DIG. 7 |
| 4,087,864 | 5/1978 | LaBove et al. | 604/174 X |
| 4,504,267 | 3/1985 | Parmelee et al. | 604/174 X |

Primary Examiner—Dalton L. Truluck
Attorney, Agent, or Firm—Reed Smith Shaw & McClay

[57] ABSTRACT

A re-usable intravenous catheter holder is provided. The holder is in the shape of a cut-off tank top body garment which is fitted securely around the patient's chest by an elastic band around the base of the garment. The holder supports a catheter tube and coupling which protrudes from the patient's chest. The design also provides a means whereby the shoulder strap of the garment may be opened to allow access to the catheter without removal of the holder, while maintaining constant shape of the holder. Also, the holder may be worn or removed by the patient without experiencing discomfort.

1 Claim, 4 Drawing Figures

INTRAVENOUS CATHETER HOLDER

FIELD OF THE INVENTION

The invention relates to devices for holding and supporting an intravenous catheter and in particular to such a device which is worn by, rather than attached to, the patient.

DISCUSSION OF THE TECHNICAL PROBLEM

In many instances it is desirable to have repeated and frequent access to a patient's circulation for the delivery of blood and intravenous solutions. Procedures have been developed in the prior art to allow such access while avoiding repreated venipuncture. One type of procedure involves the use of a Hickman catheter.

The Hickman indwelling right atrial catheter was designed some years ago by Robert O. Hickman. The Hickman catheter provides ready access to the patient's circulation both for drawing blood and for administering drugs, blood products and total paranterol nutrition. The use of the catheter can also provide added comfort and nutrition to inpatients, and outpatients can be sent home with the catheter in place to allow them the independence of administering their own parenteral nutrition.

Various methods of insertion of the Hickman catheter have been disclosed and discussed in articles entitled "Hickman Indwelling Catheter", by Jean Byeletich and Robert O. Hickman, *American Journal of Nursing*, Jan. 1980, pp. 62–65 and "Hickman Catheter Placement Simplified", Norman L. Wool, et al., *American Journal of Surgery*, Vol. 145, Feb. 1983. The technical method of insertion is beyond the scope of this discussion, however, the placement and position of the catheter after insertion is critical to the technical problem which gives rise to this invention.

The catheter is basically comprised of a long tube which is inserted into the right atrium inside the patient's chest. The tube then extends from inside the atrium to outside of the patient's chest where a coupling is attached to the outside end of the tube. The external end of the coupling is threaded and has a port through which injections or transfusions can be administered directly, allowing less chance of contamination and air embolism.

Hickman has recently developed a double catheter that is comprised of two couplings that are attached to the insertion tube. See FIG. 4. Since this catheter has two couplings attached to the end of the tube, it is somewhat heavier than the single Hickman catheter. The double catheter is rapidly becoming more popular with doctors since chemotherapy can be administered through one coupling while blood or parenteral nutrition can be administered through the other coupling at the same time.

When using either the double or single catheter, the catheter is implanted inside the patient and as such may remain implanted for months at a time. It is therefore important to provide a means of support for holding the sterile sponge, on the site where the catheter becomes exposed from the chest area and the protruding tube and coupling, since without support the tube and coupling would hang loosely down the front of the patient's chest. The common method used to support the sterile sponge and the tube and coupling is to tape the assembly directly onto the patient's skin. However, after repeatedly removing the tape to clean the sterile site and to use the catheter, the patient's skin becomes sensitive to the point that it can be extremely painful to remove or apply the support tape. It would, therefore, be desireable to provide a re-usable means of support for the catheter assembly where the assembly is not attached directly to the patient's skin.

SUMMARY OF THE INVENTION

The present invention provides a re-usable holder to support an intravenous catheter assembly. The support means is a body garment which is worn around the chest of the patient. The garment, which has the appearance of a tank top undershirt, may be worn continuously around-the-clock. It may be removed by the patient to make use of the catheter assembly or for bathing, and then put back on the patient's body. The invention eliminates the need for taping the catheter directly onto the patient's skin, thereby preventing painful removal of tape from the patient's body.

DESCRIPTION OF THE PREFERRED EMBODIMENTS

Figure 1:
FIG. 1 is a frontal view of the catheter holder.

With reference to FIG. 1, the catheter holder 1 appears to be a cut-off tank top undershirt that is comprised preferably of a cotton or other cotton blend fabric. At the bottom of the holder 1, approximately 2 inches of fabric along the back and sides and approximately 6 inches along the front, are folded inwardly around the bottom of the garment. An elastic band 2 is placed inside the holder 1 along the bottom. The elastic band 2 is then sewn into place around the bottom by stitching the fabric just above the band 2 along a line 3 around the bottom of the holder.

After sewing the band 2 in place along the bottom, the remaining 4 inches of fabric along the front is sewn along lines 4 forming a pouch 5 on the inside of the holder 1 against the patient's chest. At the top of the pouch 5, a lip is formed by folding the remaining end of the fabric around another piece of elastic 6 and then sewing the material along line 7. The upper piece of elastic 6 maintains the shape of the pouch 5.

Figure 2:
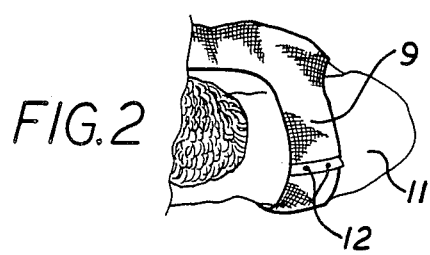
FIG. 2 is a top view of the catheter holder worn by the patient.
Figure 4:
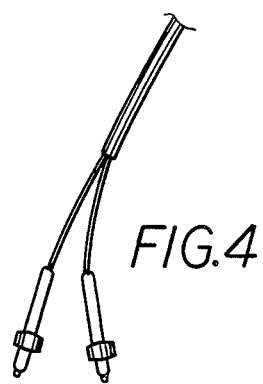
FIG. 4 is a frontal view of the Hickman indwelling double catheter.

With reference now to FIG. 2, two vertical straps 8 and 9, which form the top of the holder 1, cross the patient's shoulders 10 and 11 when the holder 1 is worn on the patient. On one of the vertical straps 9 is a pair of snaps 12 which is sewn into the fabric. The snaps 12 must be attached to the vertical strap that is on the same side of the holder 1 as the surgical site of the catheter. This is essential since when the patient changes a sterile dressing, the snaps 12 may be opened so that the strap 9 of the holder 1 may fold down to expose the catheter site without total removal of the holder 1. Also, while the vertical strap 9 is unsnapped the catheter tube and coupling may be placed in or removed from the holder's inside pouch 5. Without snap's the holder 1 may be extensively stretched while performing either of the above mentioned procedures. The snaps 12 are essential to the holder itself since by extensively stretching the holder 1, the holder's 1 functional support may be destroyed.

It is important that the straps 8 and 9 be comprised of and cut from the same material as the remainder of the holder 1. The straps 8 and 9 must not be attached separately to the holder, since when the straps and body of the holder are intergerally related the patient may move his body in any direction and still experience total longitudinal and transverse support frm the holder 1. In this manner, total support is applied to the catheter and slippage of a sterile sponge or covering is avoided as much as possible.

Figure 3:
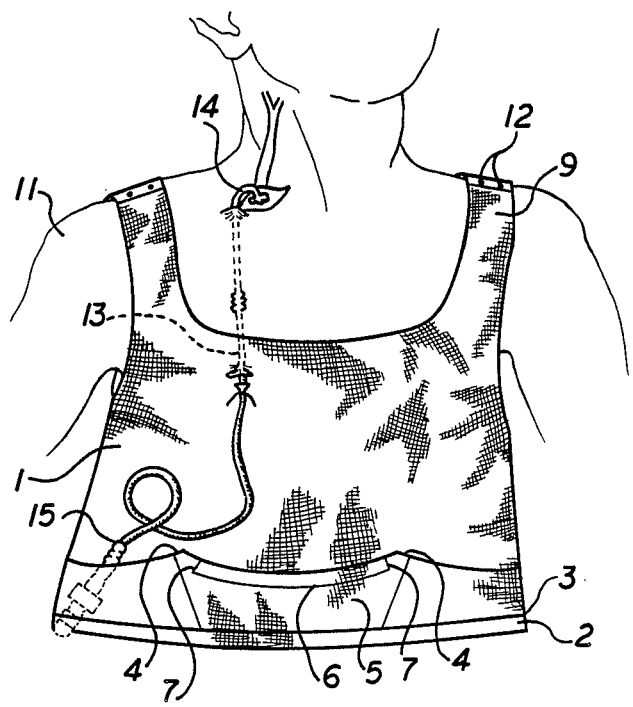
FIG. 3 is a frontal view of the catheter holder, when worn by the patient, showing the holder as it supports the catheter.

With reference now to FIG. 3, the total functional capabilities of the holder 1 may be seen. The catheter tube 13, which protrudes from a surgicval slit near the patient's neck hangs down the front of the patient's chest and a coupling 15 is attached to the end of the tube 13. By placing part of the tube 13 and the coupling 15 into the pouch 5, the holder 1 provides support for the external components of the catheter.

The present invention provides support of the catheter without causing any sensitivity to the patient's skin from application or removal of the currently used tape holders. Additionally, support is provided without pressing the catheter against the skin thereby eliminating potentially painful pressure points that were previously caused by either the catheter or tape holder. The elasticity of the hold 1 also provides reinforcement of the position of a sterile sponge or dressing.

The hold is designed to be worn twenty-four hours a day, seven days a week without causing any harm to the catheter or the patient's chest or circulation. Since the holder has the appearance of a cut-off tank top shirt, it may be worn both as an undergarment during cold weather and as a sleeveless T-shirt during warm weather. It may also be worn under other clothing without being visible while maintaining the functional and practical purposes of a catheter holder. The basic design can easily be modified to be worn by a person of varying height and weight and of either sex without changing the holder's practicality or function. Additionally the holder can be used to support either a single or double catheter.

Of course, the present invention is not to be limited to the specific embodiments described above, but rather by the claims that follow.

What is claimed is:

1. A re-usable intravenous catheter holder configured in the shape of a cut-off tank top body garment comprising:
   a. an integral frontal support pouch for holding and supporting an indwelling catheter tubing and coupling, and being disposed on the garment side adjacent the chest of the patient;
   b. an elastic band integrally disposed around the bottom of said holder;
   c. an integral shoulder strap, on the frontal side of the garment where the catheter protrudes from the patient's chest, that may be opened or closed by a fastening means wherein said fastening means may be comprised of one of:
      i. garment snaps;
      ii buttons; or
      iii. hook and loop fasteners; and
   d. a second elastic band integrally disposed along the open lip of said support pouch to maintain the shape thereof.

* * * * *